United States Patent
Torti et al.

[11] Patent Number: 6,123,905
[45] Date of Patent: *Sep. 26, 2000

[54] PIPETTOR INCLUDING AN INDICATOR AND METHOD OF USE

[75] Inventors: Victor A. Torti, Brookline; George P. Kalmakis, Reading, both of Mass.; Gary E. Nelson, Hollis, N.H.

[73] Assignee: Matrix Technologies Corporation, Hudson, N.H.

[*] Notice: This patent issued on a continued prosecution application filed under 37 CFR 1.53(d), and is subject to the twenty year patent term provisions of 35 U.S.C. 154(a)(2).

[21] Appl. No.: 08/785,511

[22] Filed: Jan. 17, 1997

[51] Int. Cl.[7] ....................................................... B01L 3/02
[52] U.S. Cl. .................. 422/100; 73/864.02; 73/864.13; 73/864.16; 422/101
[58] Field of Search ..................................... 422/100, 101; 436/54, 178, 180; 73/864.14, 864.15, 864.17, 864.18, 863.23, 863.24, 863.25, 864.01, 864.02, 864.13, 864.16

[56] References Cited

U.S. PATENT DOCUMENTS

| | | | |
|---|---|---|---|
| 4,999,164 | 3/1991 | Puchinger et al. | 422/100 |
| 5,092,184 | 3/1992 | Goodell et al. | 73/863.32 |
| 5,156,811 | 10/1992 | White | 422/100 |
| 5,364,595 | 11/1994 | Smith | 422/100 |
| 5,456,879 | 10/1995 | Suovaniemi | 422/100 |
| 5,496,523 | 3/1996 | Gazit et al. | 422/100 |

FOREIGN PATENT DOCUMENTS

WO 94/20831  9/1994  WIPO .

*Primary Examiner*—Jan Ludlow
*Attorney, Agent, or Firm*—Wolf, Greenfield & Sacks, P.C.

[57] ABSTRACT

A pipettor including a body portion, a cylinder having an interior channel, and a filter plug disposed within the channel is disclosed. The filter plug may include a plurality of pores and may preferably be treated with a first chemical, so as to affect closure of the pores when the filter plug contacts a pipetted fluid. The pore closure helps contain leakage of the fluid into the pipettor by sealing the pipettor to additional fluid flow. The filter plug may also be treated with a second chemical to affect a change in the color of the filter plug upon contact with the pipetted fluid. The color change acts as a signal to an operator that possible contamination of the pipettor has occured. The color change and/or closure may also be affected by an aerosol generated from the pipetted fluid.

7 Claims, 3 Drawing Sheets

PIPETTOR INCLUDING AN INDICATOR AND METHOD OF USE

BACKGROUND

1. Technical Field

The present application relates to pipettors and pipetting, and more particularly to a pipettor including an indicator filter.

2. Background of Related Art

Pipettors are widely utilized in laboratories for taking up and discharging precise quantities of fluid. Automated pipettors generally include a motor for actuating a piston, the piston being housed in a cylinder and open to the tip of the pipettor. Generally, two methods of pipetting are practiced, positive displacement pipetting and air displacement pipetting. In positive displacement pipetting the fluid to be pipetted is in direct contact with the base of the piston and the cylinder in which the piston moves. The piston and walls of the displacement cylinder of the pipettor are therefore exposed, or contaminated, with the fluid being pipetted, which may be unacceptable in certain applications. Positive displacement pipettors should, therefore, be regularly cleaned or should utilize disposable pistons and cylinders to avoid cross-contamination of samples.

The more common method of pipetting is the air displacement method which utilizes an air buffer between the base of the piston and the fluid present in a disposable pipette tip, which is attached to one end of the pipettor. In air displacement pipetting, the piston and cylinder in which the piston moves are not intended to be exposed to the fluid being pipetted, as the fluid is generally confined within the disposable pipette tip. Thus, the piston and cylinder need not be replaced or thoroughly cleaned after every use. Even in air displacement pipetting, however, some contamination of the piston and cylinder may occur if either the fluid itself, or aerosol from the fluid, comes into contact with the piston and/or cylinder. This can occur if the operator inadvertently overfills the disposable tip, or if the fluid is agitated in such a manner as to create aerosol fumes. In such situations the piston and/or cylinder may need to be cleaned or possibly replaced.

It some instances it may be difficult for an operator to determine if the cylinder or piston has become contaminated, especially if contamination is due to aerosols formed by the fluid. In addition, if overfilling has occurred, containing the fluid before it reaches the piston or beyond, would be desirable.

There is therefore a need in the art for a device which indicates contamination of a pipettor to an operator and which helps to limit the extent of overfilling, so as to contain such contamination.

SUMMARY

A pipettor including a body portion, a cylinder having an interior channel, and a filter plug disposed within the channel is disclosed. The filter plug may include a plurality of pores and may preferably be treated with a first chemical, so as to affect closure of the pores when the filter plug contacts a pipetted fluid, thereby sealing the channel containing the filter. The pore closure helps contain further leakage of the fluid into the pipettor by sealing the pipettor to additional fluid flow. The filter plug may also be treated with a second chemical to affect a change in the color of the filter plug upon contact with the pipetted fluid. The color change acts as a signal to an operator that possible contamination of the pipettor has occured. The color change and/or closure may also be affected by an aerosol generated from the pipetted fluid.

In one embodiment, the fluid is water or an aqueous based fluid.

In another embodiment, the cylinder includes a tip fitting configured and adapted for use with a disposable pipettor tip.

In another embodiment, the cylinder is removably attached to the body portion.

In another embodiment, the filter plug is cylindrical in shape and is friction fitted within the interior channel.

BRIEF DESCRIPTION OF THE DRAWINGS

Various embodiment are described herein with reference to the drawings, wherein.

DETAILED DESCRIPTION OF THE PREFERRED EMBODIMENTS

Figure 1:
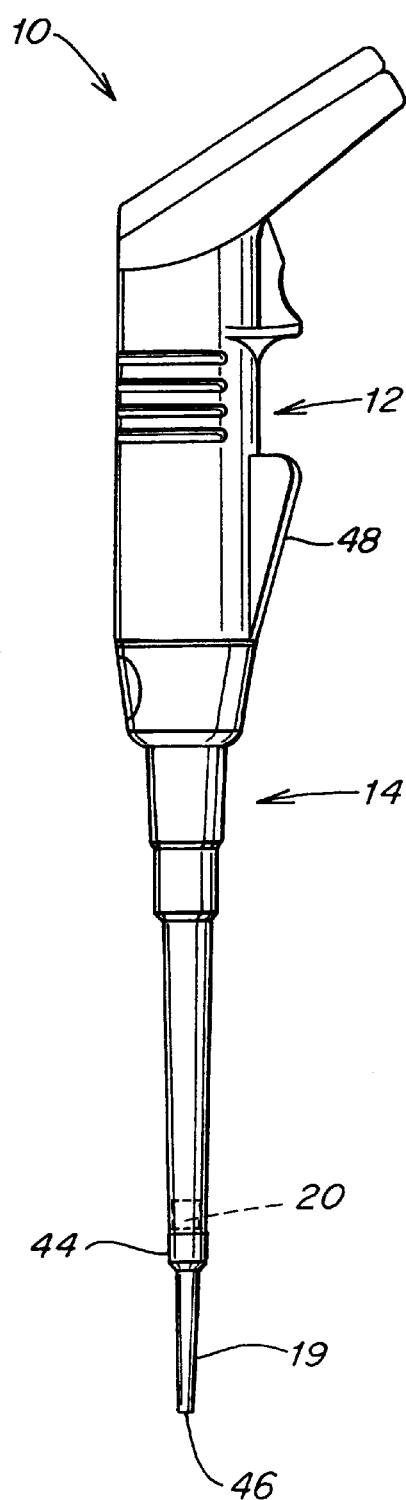
FIG. 1 is a schematic of a pipettor including a filter plug in accordance with the present invention.

Referring initially to FIG. 1, there is illustrated an automated pipettor 10 utilized for air displacement pipetting and including a body portion 12 and a cylinder 14. FIG. 1 is a representative pipettor only, the embodiment of FIG. 1 being commercially available under the brand name Impact® from Matrix Technologies Corporation, located in Lowell, Mass. It should be understood that any number of air displacement pipettor designs, whether manual or automated, and available from a variety of manufacturers, may be utilized in accordance with the present invention.

Figure 2:
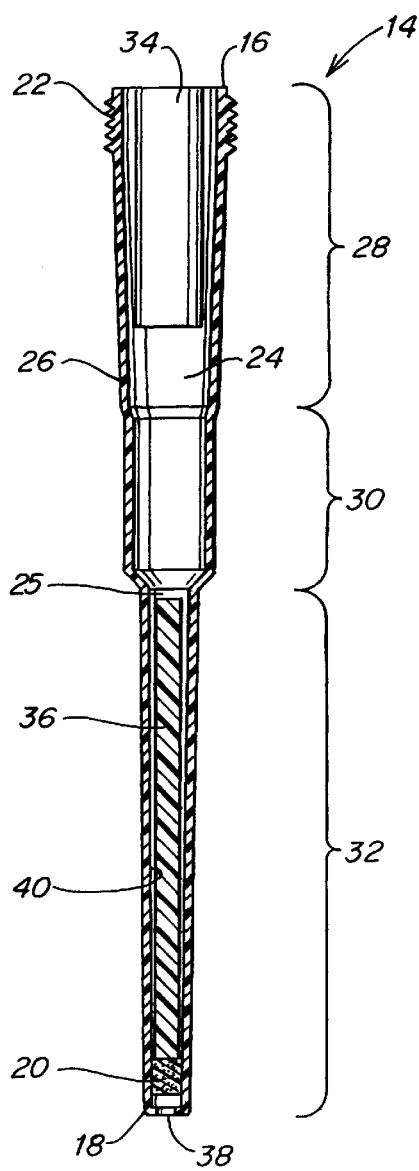
FIG. 2 is an elevation view in partial cross-section of a cylinder including a filter plug of the embodiment of FIG. 1.

With continued reference to FIG. 1 in conjunction with FIG. 2, cylinder 14 includes a first end 16 for connection to body portion 12 and a second, or tip fitting end 18 for connection to a disposable pipette tip 19, the tip fitting end including a filter plug 20 disposed therein. Cylinder 14 may be any of a number of volumes, with volumes of 12.5, 30, 125, 250, and 1250 microliters being conventional, and with a 1250 microliter pipettor being illustrated in the present embodiment. First end 16 preferably includes a threaded section 22 for engagement with corresponding threads (not shown) formed in body portion 12, for releasably securing the cylinder to the body portion. Alternately, other connection methods may be utilized, for example a bayonet connection, as is well know to one of skill in the art.

Cylinder 14 preferably defines an interior chamber 24 and a communication channel 25, for communication between the pipettor 10 and disposable tip 19. Cylinder 14 may be tapered and include an outer wall 26 having a stepped configuration, as in the illustrated embodiment. The stepped configuration of outer wall 26 may divide chamber 24 into an upper portion 28, a mid-portion 30, and a lower portion 32, all three portions being in communication with each other. Alternately, cylinder 14 may not have a stepped configuration, or may have greater than, or less than three portions defined by the stepped configuration illustrated in FIG. 2. In the present embodiment, a piston 34 may be actuated to move within chamber 24, between the upper and mid-portions 28, 30 during intaking and dispensing of fluid. The piston 34 preferably does not enter the communication channel 25 defined by lower portion 32, as the lower portion is preferably elongated, and the channel is therefore preferably smaller than the outer diameter of the piston 34.

Communication channel 25 may include a rod 36 disposed therein, the rod being made of plastic and utilized to take up dead air space, i.e. the air not used in the act of pipetting. Also disposed within channel 25, preferably adjacent tip fitting end 18 and aperture 38, is filter plug 20. In the present embodiment, filter plug 20 is configured and dimensioned to fit within communication channel 25 and may be held in place by friction between the surface of the filter plug and the interior surface 40 of the lower cylinder portion. Alternately, other devices for taking up dead air space, may be utilized, for example, filter plug 20 may be configured and dimensioned to take up the dead air space, as well as performing as an indicator and containment device.

Figure 3:
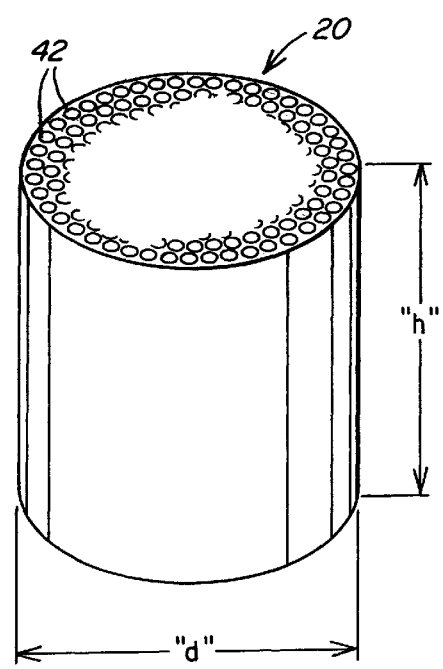
FIG. 3 is an enlarged, perspective view of the filter plug of the embodiment of FIG. 1.

Referring now to FIG. 3, the filter plug 20 may be cylindrically shaped, and preferably is approximately ⅛ to ¼ of an inch in height, "h", and approximately 1/16 to ¼ of an inch in diameter, "d". For use in a 1250 μl pipettor, filter plug 20 is approximately ¼ of an inch in height and approximately ⅕ of an inch in diameter. It should be understood that other shapes and sizes are contemplated, provided, however, that the filter plug 20 should be configured and dimensioned to fit within tip section 32. In the present embodiment, the filter plug 20 may be made of a sintered polyethylene material available from General Polymeric of Reading, Pa., the material preferably including a plurality of pores, as partially represented by pores 42. Filter plug 20 is preferably treated with a first chemical during compounding and prior to molding, to affect closure of the pores, and may additionally be treated with a second chemical preferably after molding, to affect color change of the plug, both chemicals reacting when the filter plug contacts water or any aqueous fluid. The color change and/or closure may also be affected by an aerosol generated from the aqueous fluid, in the present embodiment. It should be understood that filter plug 20 is preferably chemically treated to react with aqueous fluids because these fluids represent the majority of fluids pipetted. Filter plug 20 may, however, be chemically treated to react to any of a variety of fluids or chemicals, depending upon the desired application. In addition, the filter plug 20 may be treated with either or both of the chemicals, such chemically treated, sintered polyethylene materials also being available from General Polymeric.

Filter plug 20 preferably is composed of a porous, sintered polyethylene material, the sintered polyethylene material being hydrophobic. Prior to contacting water or an aqueous fluid, the plurality of pores 42 allow fluid and air to pass therethrough. Before molding, as part of the compounding process, the polyethylene material is treated with a first, hydrophilic chemical, so that upon contact of the fluid with plug 20, the fluid passes through the pores and initiates a reaction with the first chemical. This reaction causes the first chemical to close off pores 42 and prevents any further fluid from passing through the plug and into cylinder 14. The filter plug 20 thus acts to contain the fluid and may prevent fluid from contacting the tip of the piston 34, depending upon the amount of fluid which has passed through the filter, and the position of the piston. Filter plug 20 may, additionally, be treated with a second chemical which affects the color of the plug, when the plug contacts the fluid.

Filter plug 20 may preferably be treated with a second chemical, the filter plug being a first color, prior to contact with the fluid. The chemical utilized may selectively change the first color to a second color, upon contact with the fluid, or aerosols generated from the fluid. In the present embodiment, filter plug 20 is preferably treated with a cobalt-chloride which turns the plug a light-blue color, prior to contact with the fluid. Upon contact with water, or any aqueous fluid, the light-blue color changes to a pink color. Alternate chemical treatments and/or colors may be utilized as is known to one skilled in the art. In addition, the first color may be white or clear and the second color may be a shade of the first color. Thus, if during pipetting, fluid inadvertently enters channel 25 through aperture 38, for example by overfilling, the fluid will contact the filter plug 20 and affect a change in color of the filter. This change in color acts as a notification to the operator that the cylinder has contacted the fluid, and that contamination may have, therefore occurred.

In operation, a laboratory technician will choose an appropriate size pipettor 10, the pipettor having a filter plug 20 disposed within communication channel 25. The technician will then choose a disposable tip 19 having a head portion 44 at one end thereof and an aperture 46 at an opposite end thereof, and fit the head portion over the tip fitting end 18, such that aperture 46 is in communication with cylinder 14. The technician is now ready to pipette.

Figure 4:
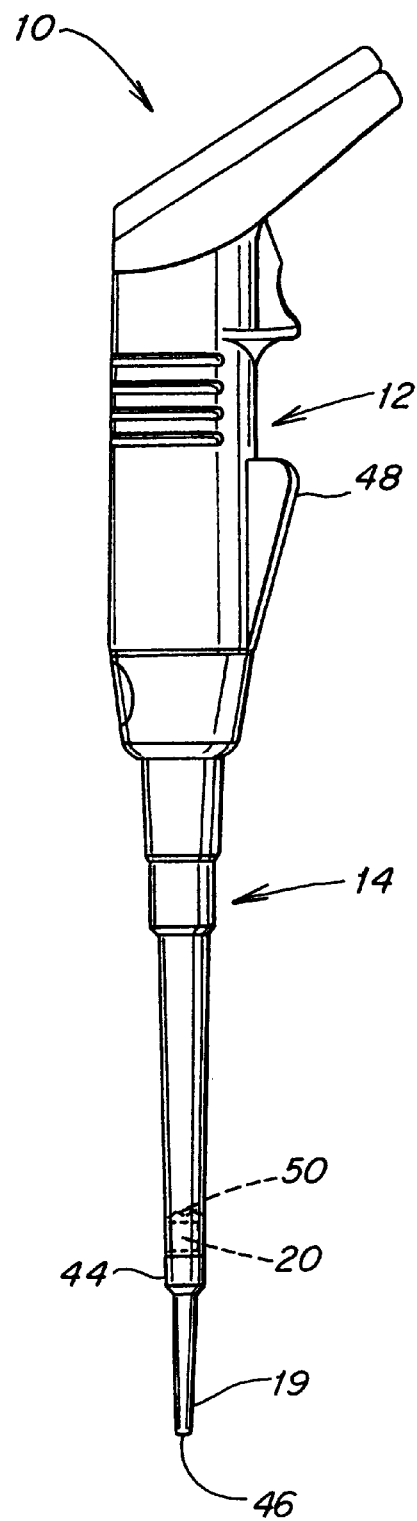
FIG. 4 is a schematic of a pipettor containing fluid which has been pipetted and which has passed through the filter plug of the embodiment of FIG. 1 and into the cylinder.

The technician then places disposable pipette tip 19 into a container holding a sample fluid to be pipetted and may input the volume intended to be pipetted, if the pipettor is so designed. The technician then depresses trigger 48 to engage a motor (not shown) disposed within body portion 14, and the motor actuates piston 34. Upon actuation of piston 34, the fluid is drawn into disposable pipette tip 19, and preferably fills the tip to the desired amount. If, however, the fluid overfills tip 19, fluid will enter cylinder 14 through aperture 38, into channel 25 and contact filter plug 20. In the illustrated embodiment, upon contact of an aqueous fluid with filter plug 20, the plug begins to change color from blue to pink and also begins to block its pores 42. As suggested in FIG. 4, once the filter pores are blocked, fluid 50 is trapped above the filter plug, and no further fluid may flow into the cylinder 14, as the filter plug has been sealed against fluid flow. Thus, filter plug 20 operates as a visual indicator to the operator of possible contamination by changing color and/or operates to prevent further contamination of the cylinder 14 and/or piston 34 by preventing additional fluid from entering the cylinder.

It will be understood that various modifications may be made to the embodiment disclosed herein. For example, the filter plug may be treated to only change color and may not block fluid entry, or may only block fluid entry and not change color. In addition, although a single channel pipette is illustrated, the filter plug may be inserted into a channel or tip fitting end of a multi-channel pipettor as well. Therefore, the above description should not be construed as limiting, but merely as exemplifications of preferred embodiments. Those skilled in the art will envision other modifications within the scope and spirit of the claims appended hereto.

What is claimed is:

1. In combination:

a pipettor, comprising:

a body portion having a cylinder fitting end;

a cylinder attached to the cylinder fitting end of the body portion, the cylinder having a tip fitting end and defining an interior chamber, the chamber having a cross-sectional area adjacent the tip fitting end, the tip fitting end having an opening with a cross-sectional area less than the cross-sectional area of the chamber adjacent the tip fitting end;

a piston, the piston moving within the interior chamber of the cylinder and the body portion; and a filter plug disposed in the interior chamber of the cylinder between the opening and the piston, said filter plug having a cross-sectional area substantially equal to the cross-sectional area of the chamber adjacent the tip fitting end; and a pipette tip having an upper end and a lower end, and being in fluid communication at the upper end with the opening in the tip fitting end of the cylinder, the pipette tip and tip fitting end of the cylinder defining an unobstructed interior channel extending from the filter plug through the opening to the lower end of the pipette tip.

2. The combination of claim 1, wherein the cylinder is detachably connected to both the cylinder fitting end of the body portion and the pipette tip.

3. The combination of claim 1, wherein the filter plug is disposed adjacent the opening.

4. The combination of claim 3, wherein the filter plug is spaced apart from the pipette tip to define a space between the filter plug and the pipette tip.

5. The combination of claim 1, wherein at least a portion of the filter plug is changeable from a first color to a second color upon a fluid or an aerosol contacting the filter plug.

6. The combination of claim 5, wherein the filter plug includes a plurality of pores and a material which blocks the plurality of pores to fluid flow upon a fluid or aerosol contacting the filter plug.

7. The combination of claim 1, wherein the filter plug includes a plurality of pores and a material which blocks the plurality of pores to fluid flow upon a fluid or aerosol contacting the filter plug.

\* \* \* \* \*